United States Patent [19]

Klaus et al.

[11] Patent Number: 5,391,766
[45] Date of Patent: Feb. 21, 1995

[54] ALKYL OR ALKOXY SUBSTITUTED S-HETEROCYCLIC RETINOIDS

[75] Inventors: Michael Klaus, Weil/Rhein, Germany; Peter Mohr, Basel, Switzerland

[73] Assignee: Hoffmann-La Roche Inc., Nutly, N.J.

[21] Appl. No.: 57,949

[22] Filed: May 5, 1993

[30] Foreign Application Priority Data

May 7, 1992 [CH] Switzerland .................. 1465/92

[51] Int. Cl.⁶ .................. C07D 335/06; A61K 31/38
[52] U.S. Cl. .................................................. 549/23
[58] Field of Search .................. 549/23; 514/432

[56] References Cited

U.S. PATENT DOCUMENTS

| | | | |
|---|---|---|---|
| 4,678,793 | 7/1987 | Klaus et al. | 514/311 |
| 4,788,213 | 11/1988 | Klaus et al. | 514/432 |
| 4,810,804 | 3/1989 | Chandraratna | 514/432 |
| 4,833,254 | 5/1989 | Berlin et al. | 548/454 |
| 5,037,825 | 8/1991 | Klaus et al. | 514/432 |

OTHER PUBLICATIONS

Apfel et al., "A retinoic acid receptor α antagonist selectively counteracts retinoic acid effects", Proc. Natl. Acad. Sci USA, vol. 89, #15 (Aug. 1, 1992) pp. 7129–7133.
Frierson, et al., "Computer–Automated Structure Evaluation of Retinoids in Teratogenesis Bioassays", Fundam. Appl. Toxicol, 14, pp. 408–428 (1990).
Lehmann, et al., "Identification of Retinoids with Nuclear Receptor Subtype-Selective Activities", Cancer Research, 51, pp. 4804–4809, (1991).

*Primary Examiner*—Glennon H. Hollrah
*Assistant Examiner*—Mary C. Cebulak
*Attorney, Agent, or Firm*—George M. Gould; William H. Epstein; Bruce A. Pokras

[57] ABSTRACT

Compounds of the formula

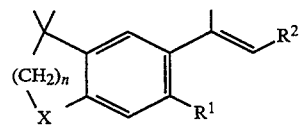

I in which X is —S—, —SO— or —SO$_2$—; R$^1$ is C$_{7-10}$-alkyl or C$_{7-10}$-alkoxy; R$^2$ is a residue of the formula

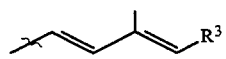

(a)

or

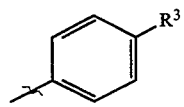

(b)

R$^3$ is carboxy or lower-alkoxycarbonyl; and n is an integer of 1, 2 or 3; and salts of carboxylic acids of formula I can be used for the treatment of autoimmune diseases and diseases having a strong immunological component, such as psoriasis.

15 Claims, No Drawings

ALKYL OR ALKOXY SUBSTITUTED S-HETEROCYCLIC RETINOIDS

SUMMARY OF THE INVENTION

The present invention is concerned with novel alkyl or alkoxy substituted S-heterocyclic compounds of the formula:

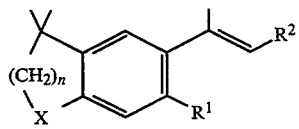  I in which X is —S—, —SO— or —SO$_2$—;
R$^1$ is C$_{7\text{-}10}$-alkyl or C$_{7\text{-}10}$-alkoxy;
R$^2$ is a residue of the formula

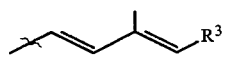 (a)

or

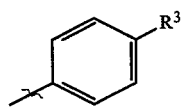 (b)

R$^3$ represents carboxy or lower-alkoxycarbonyl; and n is an integer from 1 to 3;
as well as salts thereof where R$^3$ is carboxy.

The invention is also concerned with pharmaceutical preparations based on the compounds of formula I or their salts and with a process for the manufacture of the compounds I.

DETAILED DESCRIPTION OF THE INVENTION

The term "lower" used herein denotes groups with up to 6 carbon atoms. Preferred lower groups contain 1–4 carbon atoms, such as, for example, methyl, ethyl, isopropyl or 2-methylpropyl.

The terms C$_{7\text{-}10}$-alkyl and C$_{7\text{-}10}$-alkoxy denote alkyl and alkoxy groups with 7–10 carbon atoms, such as heptyl, octyl, nonyl and decyl.

A preferred group of compounds of formula I comprises those in which R$^1$ is heptyl, octyl, heptyloxy or octyloxy; R$^3$ is carboxyl and X=SO$_2$.

The compounds of formula I can be obtained by
a) reacting a compound of the formula

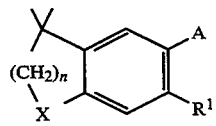 II with a compound of the formula

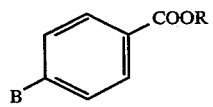 III

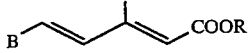 IV wherein R is lower-alkyl and either A is a triphenylphosphoniumethyl group

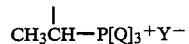

or dialkoxyphosphinylethyl group

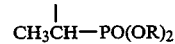

and B is formyl; or A is acetyl and B is a triphenylmethylphosphonium group —CH$_2$—P[Q]$_3$$^+$Y$^-$ or a dialkoxyphosphinylmethyl group —CH$_2$—PO(OR)$_2$; and Q is phenyl; or by
b) reacting a compound of the formula

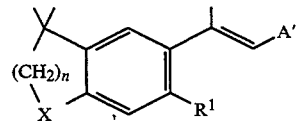 V with a compound of the formula

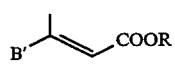 VI wherein either A' is a triphenylmethylphosphonium group —CH$_2$—P$^+$[Q]$_3$Y$^-$ or a dialkoxyphosphinylmethyl group —CH$_2$—PO(OR)$_2$ and B' is formyl; or A' is formyl and B is a triphenylmethylphosphonium group —CH$_2$—P$^+$[Q]$_3$Y$^-$ or a dialkoxyphosphinylmethyl group —CH$_2$PO(OR$_2$) and n, Q and R have the significance given above,
to give a compound of formula I in which R$^3$ is —COOR and, if desired, saponifying the ester group —COOR and isolating the carboxylic acid obtained as such or as a salt; and/or oxidizing a compound of formula I obtained in which X is —S— to a compound of formula I in which X is —SO— or —SO$_2$—.

The reaction of the compound II with the compounds III or IV and the reaction of the compound V with the compound VI can be carried out according to methods which are known per se for the Wittig or Horner reaction.

The reaction of compounds having triphenylphosphonium groups (Wittig reaction) can be effected in the presence of an acid-binding agent, e.g. a strong base such as e.g. butyllithium, sodium hydride or the sodium salt of dimethyl sulphoxide, but primarily in the presence of an ethylene oxide which is optionally substituted by lower alkyl, such as 1,2-butylene oxide, optionally in a solvent, e.g. in an ether such as diethyl ether or tetrahydrofuran or in an aromatic hydrocarbon such as benzene, in a temperature range lying between room temperature and the boiling point of the reaction mixture.

Examples of anions Y$^-$ in the Wittig reagent are Cl$^-$, Br$^-$, HSO$_4$$^-$ and tosylate.

The reaction of compounds having dialkoxyphosphinyl groups (Horner reaction) can be carried out in the presence of a base and, preferably, in the presence of an inert organic solvent, e.g. in the presence of sodium hydride in benzene, toluene, dimethylformamide, tetrahydrofuran, dioxan or a 1,2-dimethoxyalkane, or also a sodium alcoholate in an alkanol, e.g. sodium methylate in methanol, in a temperature range between 0° and the boiling point of the reaction mixture.

A thus-obtained carboxylic acid ester of formula I can be hydrolyzed in a manner known per se, e.g. by treatment with alkalis, especially by treatment with aqueous-alcoholic sodium or potassium hydroxide solution in a temperature range lying between room temperature and the boiling point of the reaction mixture.

The thus-obtained carboxylic acid of formula I can be isolated in a manner known per se as such or as a salt, e.g. as an alkali salt, especially as the Na or K salt.

A compound of formula I in which X stands for —S— can be oxidized using methods known per se to a compound of formula I in which X stands for —SO— or —SO$_2$—. The oxidation can be carried out using oxidation agents such as periodates, e.g. NaIO$_4$, or using organic peracids such as m-chloroperbenzoic acid. About one equivalent of peracid is used in the oxidation using organic peracids in order to obtain a sulphoxide compound (X=SO), whereas the use of two equivalents of peracid leads to sulphones (X=SO$_2$).

The compounds of formula I can be present as double bond isomers. They generally occur in the trans or all-trans form in the process. Cis isomers which may occur can be isolated from the mixture in a manner known per se where required.

The starting materials of formulae II–VI are known or can be prepared in analogy to the known compounds or according to methods described in the following Examples.

The preferred compounds of this invention have the following formulas:

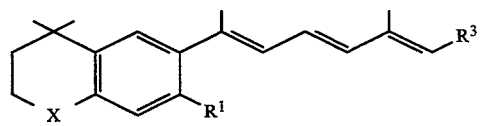
I-A

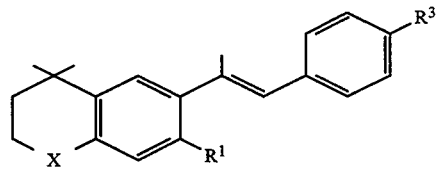
I-B

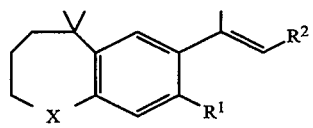
I-C

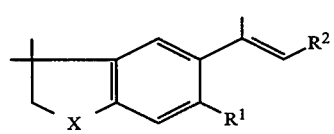
I-D wherein R$^1$, R$^2$, R$^3$ and X are as above.

Among the preferred compounds of formula I-D are those compounds where R$^2$ is

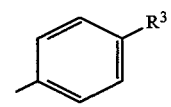
I-E and R$^3$ is as above; as well as those compounds of formula I-D where X is —SO$_2$— and R$^2$ is R-E. Also preferred as those compounds or formula I-C wherein X is SO$_2$.

The compounds of formula I are retinoic acid α-receptor (RARα-receptor) inhibitors. It has been found that the compounds of formula I suppress retinoid-induced malformations. The compounds of formula I can therefore be used for the prevention of teratogenic effects which can occur during the therapeutic use of retinoids.

Furthermore, the compounds of formula I can be used for the treatment and prevention of disease states which can be caused by an over-regulation of the RARα-receptor. Among these diseases are autoimmune diseases or other disorders having a strong imunological component such as e.g. psoriasis or other dermatological conditions.

Also included in this invention are salts of these compounds of formula I wherein R$^3$ is carboxyl above with pharmaceutically acceptable, non-toxic, inorganic or organic bases, e.g., alkali metal and alkaline earth metal salts. Among the preferred salts are the sodium, potassium, magnesium or calcium salts, as well as salts with ammonia or suitable non-toxic amines, such as lower alkyl amines, for example triethylamine, hydroxy-lower alkylamines, for example 2-hydroxyethylamine, bis-(1-hydroxyethyl)amine or tris-(2-hydroxyethyl)-amine, cycloalkylamines, for example dicyclohexylamine, or benzylamines, for example N,N'-dibenzylethylenediamine, and dibenzylamine. These salts can be prepared by treating the compounds of formulae I and II, where R$_9$ is hydrogen with inorganic or organic bases by conventional means well known in the art.

In view of their activity, the compounds of formula I as well as salts thereof are effective as disease modifiers for treating rheumatoid arthritis as well as related disorders such as osteoarthritis. The compounds of formula I and II also have activity as immunosuppressants.

The compounds of formula I and salts thereof can be utilized to treat patients suffering from rheumatoid arthritis and related disorders. In such cases, the compounds modify the effects of these diseases by reducing destruction of the bone joints caused by this disease as well as reducing inflammation, heat and pain of the bone joints which results from rheumatoid arthritis and related disorders. The compounds of formula and salts thereof are also useful for treating diseases resulting from immune hyperactivity such as transplantation autoimmunity, autoimmune disease and graft versus host disease. The unexpected lack of toxicity of the compounds of this invention increases their ability in treating these diseases.

The compounds of formula I and their salts can be used in the form of pharmaceutical preparations.

The preparations for systemic use can be produced e.g. by adding a compound of formula I or a salt thereof as the active ingredient to non-toxic inert solid or liquid carriers which are usual in such preparations.

The preparations can be administered enterally, parenterally or topically. Preparations in the form of tablets, capsules, dragées, syrups, suspensions, solutions and suppositories are e.g. suitable for enteral administration.

Preparations in the form of infusion or injections solutions are suitable for parenteral administration.

For enteral and parenteral administration the compounds of formula I can be administered to adults in amounts of about 1–100 mg, preferably 5–30 mg/day.

For topical use the active substances are conveniently used in the form of salves, tinctures, creams, solutions, lotions, sprays, suspensions and the like. Salves and creams as well as solutions are preferred. These preparations designed for topical use can be produced by mixing the active ingredients with non-toxic, inert solid or liquid carriers which are suitable for topical treatment and which are usual in such preparations.

For topical use there are conveniently suitable about 0.1–5%, preferably 0.3–2%, solutions as well as about 0.1–5%, preferably 0.3–2%, salves or creams.

If desired, an antioxidant, e.g. tocopherol, N-methyl-γ-tocopheramine as well as butylated hydroxyanisole or butylated hydroxytoluene, can be admixed with the preparations.

The following abbreviations are used in the Examples which follow and which illustrate the present invention in more detail:

DMF dimethylformamide
DMSO dimethyl sulphoxide
THF tetrahydrofuran
RT room temperature
m.p. melting point
i.v in a vacuum
EtOEt diethyl ether
tBuOH tert.-butanol
AcOEt ethyl acetate

EXAMPLE 1 a) 14.9 g of NaH, 50% in paraffin oil, were washed twice with pentane, dried in a water-jet vacuum and suspended in 60 ml of DMF. A solution of 64.8 g of 3-heptyloxyphenol in 320 ml of DMF was added dropwise thereto while cooling with ice. After stirring at 0° C. for 45 minutes a solution of 42.3 g of dimethyl-thiocarbamoyl chloride in 100 ml of DMF was slowly added dropwise to this reaction mixture and the mixture obtained was stirred at room temperature overnight. Thereafter, it was poured on to ice-water, acidified with 6N hydrochloric acid and extracted with AcOEt. The organic phase was washed with water, saturated NaHCO₃ solution and H₂O, dried over sodium sulphate and evaporated. After filtration of the crude product over a silica gel column (eluent hexane/AcOEt=4:1) there were obtained 86.7 g of O-(3-heptyloxyphenyl)dimethylthiocarbamate as a pale yellow oil.

b) 80 g of O-(3-heptyloxyphenyl)dimethylthiocarbamate in 20 g portions were heated to 260° C. for 8 hours in a metal bath. The thus-obtained S-(3-heptyloxyphenyl)dimethylthiocarbamate was used in the next step without further purification.

c) 10 g of LiAlH₄ were suspended in 200 ml of THF and treated dropwise at 0° C. with a solution of 77 g of S-(3-heptyloxyphenyl)dimethylthiocarbamate in 200 ml of THF. After stirring at room temperature for 1 hour a solution of 46.5 g of 3,3-dimethylallyl bromide in 200 ml of THF was added dropwise thereto and the mixture was stirred for a further 45 minutes. The reaction mixture was subsequently poured into an ice-water/6N hydrochloric acid mixture and extracted with EtOEt. After washing, drying and evaporation there was obtained a dark oily crude product which, after filtration over a silica gel column (eluent hexane/AcOEt=9:1), gave 64 g of heptyl m-[(3-methyl-2-butenyl)thio]phenyl ether as a yellow oil.

d) 76.9 g of heptyl m-[(3-methyl-2-butenyl)thio]phenyl ether were dissolved in 1.5 l of toluene, treated with 55 g of p-toluenesulphonic acid and heated on a water separator for 20 hours. The cooled reaction mixture was diluted with AcOEt, washed twice with dilute sodium bicarbonate solution and water, dried and evaporated. There was obtained a yellow oil which consisted of 3 parts of 7-(heptyloxy)-3,4-dihydro-4,4-dimethyl-2H-1-benzothiopyran and of 1 part of 5-(heptyloxy)-3,4-dihydro-4,4-dimethyl-2H-1-benzothiopyran. Column chromatography (silica gel, eluent hexane/1% AcOEt) gave 48.6 g of pure 7-(heptyloxy)-3,4-dihydro-4,4-dimethyl-2H-1-benzothiopyran as a pale yellow oil.

e) 4.8 ml of acetyl chloride were dissolved in 80 ml of methylene chloride and treated portionwise at 0° C. with 9.1 g of aluminium chloride. After stirring at 0° C. for 30 minutes a solution of 20.7 g of 7-(heptyloxy)-3,4-dihydro-4,4-dimethyl-2H-1-benzothiopyran in 70 ml of methylene chloride was added dropwise thereto, the mixture was stirred at 0° C. for 2 hours, poured on to ice-water and extracted with ether. After washing with water, drying and evaporation the crude product was recrystallized from hexane and there were obtained 15.5 g of 6-acetyl-7-(heptyloxy)-3,4-dihydro-4,4-dimethyl-2H-1-benzothiopyran in colourless crystals, m.p. 69°–71° C.

f) 14 g of 6-acetyl-7-(heptyloxy)-3,4-dihydro-4,4-dimethyl-2H-1-benzothiopyran were dissolved in 200 ml of chloroform and treated dropwise at 0° C. with a solution of 8.5 g of m-chloroperbenzoic acid (85%) in 120 ml of chloroform. After stirring at 0° C. for 2 hours a further 8.5 g of m-chloroperbenzoic acid in 120 ml of chloroform were added dropwise. The reaction mixture was stirred at 0° C. overnight, poured into ice-water/dilute sodium chloride solution and extracted with methylene chloride. The organic phase was washed twice with water, dried and evaporated. After filtration of the crude product over a silica gel column (eluent hexane/AcOEt=4:1) and recrystallization from AcOEt there were obtained 12.5 g of 7-(heptyloxy)-3,4-dihydro-4,4-dimethyl-2H-1-benzothiopyran-6-yl methyl ketone 1,1-dioxide in colourless crystals, m.p. 92°–93° C.

g) 3 g of sodium hydride (50% in mineral oil) were washed twice with pentane, dried in a water-jet vacuum and suspended in 50 ml of abs. DMSO. A solution of 19.3 g of diethyl (4-carbethoxybenzyl)phosphonate in 100 ml of abs. DMSO was slowly added dropwise thereto at room temperature. After stirring at room temperature for 2 hours the mixture was treated dropwise with a solution of 10.5 g of 7-(heptyloxy)-3,4-dihydro-4,4-dimethyl- 2H-1-benzothiopyran-6-yl methyl ketone 1,1-dioxide in 50 ml of abs. DMSO and the mixture obtained was stirred at 40° C. for a further 2 hours. After cooling the reaction mixture was poured on to ice-water, acidified with 2N hydrochloric acid and extracted with ethyl acetate. The organic phase was washed with water, dried over sodium sulphate and evaporated. The oily dark orange residue was filtered over a silica gel column (eluent hexane/AcOEt=2:1) and gave 13.5 g of ethyl p-[(E,Z)-2-[3',4'-dihydro-4',4'-dimethyl-7'-(heptyloxy)-2'H-1-benzothiopyran-6'-yl]propenyl]benzoate 1',1'-dioxide as a yellow oil (E/Z ratio about 1:1).

EXAMPLE 2

13.5 g of ethyl p-[(E,Z)-2-[3',4'-dihydro-4',4'-dimethyl-7'-(heptyloxy)-2'H-1-benzothiopyran-6'-yl]propenyl]benzoate 1',1'-dioxide were dissolved in 250 ml of ethanol and treated with a solution of 14.6 g of potassium hydroxide in 100 ml of water. After stirring at 50° C. for 3 hours the reaction mixture was poured on to ice-water, acidified with 3N hydrochloric acid and extracted with AcOEt. The organic phase was washed with water, dried and evaporated. The residue was recrystallized from ethyl acetate/hexane and gave 10.2 g of an E/Z mixture of the corresponding acids. By preparative HPLC (reverse phase, eluent hexane/THF=9:1+0.1% acetic acid) there were obtained, after recrystallization from AcOEt/hexane, 4.1 g of p-[(E)-2-[3',4'-dihydro-4',4'-dimethyl-7'-(heptyloxy)-2'H-1-benzothiopyran-6'-yl]propenyl]benzoic acid 1',1'-dioxide in colourless crystals, m.p. 168°–169° C., as well as 5.2. g of p-[(Z)-2-[3',4'-dihydro-4',4'-dimethyl-7'-(heptyloxy)-2'H-1-benzothiopyran-6'-yl]propenyl]benzoic acid 1',1'-dioxide, m.p. 176°–178° C.

The Z compound can be converted by irradiation in THF with a Hg high pressure lamp into a 1:1 mixture of the E/Z isomers from which further pure E compound can be obtained by preparative HPLC.

EXAMPLE 3 a) 13.6 g of 6-acetyl-7-(heptyloxy)-3,4-dihydro-4,4-dimethyl-2H-1-benzothiopyran were dissolved in 270 ml of THF. 164 ml of a 1 molar solution of vinylmagnesium bromide in THF were added dropwise thereto at −15° C. and the mixture was stirred at room temperature overnight. The reaction mixture was subsequently poured into ice-cold saturated ammonium chloride solution, extracted with EtOEt, washed with water, dried and evaporated. There was obtained a yellow-brown oil which was immediately dissolved in 270 ml of acetonitrile and treated portionwise while stirring with 16.3 g of triphenylphosphine hydrobromide. After stirring the reaction mixture at 50° C. for 2.5 hours it was evaporated and the residue was dissolved in 500 ml of ethanol (80%) and extracted repeatedly with hexane. The ethanolic solution was evaporated and the residue was dissolved in methylene chloride. After drying over sodium sulphate the solution was again evaporated and the foam-like residue was stirred with hexane for several hours, the crystalline precipitate which formed in the meanwhile was filtered off, washed with hexane and dried at 50° C. in a high vacuum. There were obtained 26.6 g of 3-[(E)-(7-heptyloxy-3,4-dihydro-4,4-dimethyl-2H-1-benzothiopyran-6-yl)-2-butenyl]triphenylphosphonium bromide, m.p. 88° C. (decomposition).

b) 25 g of the phosphonium salt obtained in a) were dissolved in 250 ml of THF and treated dropwise at −20° C. with 25 ml of butyllithium, 1.6 molar in hexane. After 15 minutes a solution of 6.3 g of ethyl (E)-3-formyl-crotonate in 30 ml of THF was added dropwise to the red-brown reaction mixture and the mixture obtained was stirred at room temperature for a further 45 minutes. It was then poured into 500 ml of a methanol/water mixture (6:4), extracted repeatedly with hexane, the non-aqueous phase was washed 3 times with water, dried and evaporated. The yellow oily residue was dissolved in 500 ml of acetonitrile and, after the addition of 560 mg of triphenylphosphine, treated with 28 ml of 0.125% solution of palladium(II) nitrate in acetonitrile. The mixture was heated to 50° C. for 5 hours, subsequently evaporated and the crude product was filtered over a short silica gel column (eluent hexane/1% AcOEt). There were obtained 13.7 g of a yellow oil which consisted of a mixture of the corresponding (4Z, 6Z), (all-E) and (6Z) compound. The further separation was effected by medium pressure chromatography using Lobar finished columns (Merck) (eluent hexane/3% AcOEt) and gave 6.6 g of ethyl (all-E)-7-[7-heptyloxy-3,4-dihydro-4,4-dimethyl-2H-1-benzothiopyran-6-yl]-3-methyl-octa-2,4,6-trienoate as a yellow oil.

EXAMPLE 4

500 mg of the (all-E) ethyl ester obtained in Example 3 were dissolved in 20 ml of ethanol and treated with a solution of 560 mg of potassium hydroxide in 10 ml of water. After 3 hours at 50° C. the clear yellow solution was poured on to ice-water, acidified with cold 3N hydrochloric acid and extracted with AcOEt. After drying and evaporation the crude product was recrystallized from AcOEt/hexane and there were obtained 150 mg of (all-E)-7-[7-heptyloxy-3,4-dihydro-4,4-dimethyl-2H-1-benzothiopyran-6-yl]-3-methyl-2,4,6-octatrienoic acid as yellow crystals, m.p. 158°–160° C.

EXAMPLE 5

Oxidation of the (all-E) ethyl ester obtained in Example 3 with 1 equivalent of m-chloroperbenzoic acid at 0° C. in chloroform as the solvent gave ethyl (all-E)-7-[7-heptyloxy-1-oxo-3,4-dihydro-4,4-dimethyl-2H-1-benzothiopyran-6-yl]-3-methyl-octa-2,4,6-trienoate as a yellow oil which was converted by hydrolysis in analogy to Example 4 into (all-E)-7-[7-heptyloxy-1-oxo-3,4-dihydro-4,4-dimethyl-2H-1-benzothiopyran-6-yl]-3-methyl-octa-2,4,6-trienoic acid. Melting point 195°–197° C. (from AcOEt/hexane).

EXAMPLE 6

Oxidation of the (all-E) ethyl ester obtained according to Example 3 with 2.2 equivalents of m-chloroperbonzoic acid at 0° C. in chloroform gave, after recrystallization from hexane, ethyl (all-E)-7-[7'-(heptyloxy)-3',4'-dihydro-4',4'-dimethyl-2'H-1-benzothiopyran-6'-yl]-3-methyl-2,4,6-octatrienoate 1',1'-dioxide, m.p. 105°–107° C. Hydrolysis of this compound in analogy to Example 4 gave, after recrystallization from AcOEt/hexane, (all-E)-7-[7-(heptyloxy)-3',4'-dihydro-4',4'-dimethyl-2'H-1-benzothiopyran-6'-yl)-3-methyl-2,4,6-octatrienic acid 1',1'-dioxide, m.p. 140°–141° C.

EXAMPLE 7 a) A solution of 10 g of m-hydroxybenzaldehyde in 100 ml of DMF was added dropwise at 0° C. to a suspension of 4 g of sodium hydride (50% in mineral oil) in 50 ml of DMF. The mixture was stirred at 0° C. for a further hour and subsequently a solution of 11.1 g of dimethylthiocarbamoyl chloride in 150 ml of DMF was added dropwise thereto. The mixture was stirred at room temperature overnight, poured on to ice-water, acidified with 6N hydrochloric acid and extracted with AcOEt. After drying the organic phase, evaporation and filtration of the crude product over a silica gel column (eluent hexane/AcOEt=3:1) there were obtained 10.2 g of O-(3-formylphenyl)dimethylthiocarbamate as a yellowish oil. This product was heated to 230° C. for 8 hours under argon in a metal bath and gave, after filtration over a silica gel column (eluent hexane/AcOEt=4:1, then 1:1) and recrystallization from EtOEt at −78° C., 7.3 g of S-(3-formylphenyl)dimethylthiocarbamate in golden yellow crystals, m.p. 76°–77° C.

b) 13.2 g of n-heptyltriphenylphosphium bromide were suspended in 200 ml of THF and treated dropwise at −10° C. with 30 ml of n-butyllithium, 1.6 molar in hexane. After stirring at 0° C. for 1 hour there was obtained a clear red solution to which a solution of 6 g of S-(3-formylphenyl)dimethylthiocarbamate in 100 ml of THF was added dropwise. The reaction mixture was stirred at room temperature for 2 hours, poured into a methanol/water mixture (6:4) and extracted with hexane. The non-aqueous phase was washed repeatedly with water, dried and evaporated. After filtration over a silica gel column (eluent hexane/AcOEt=9:1) there were obtained 6.5 g of S-(3-(1-octenylphenyl)dimethylthiocarbamate as a colourless oil (E/Z ratio about 1:2). 3 g of this product were dissolved in 250 ml of glacial acetic acid and, after the addition of 6 g of platinum/charcoal (5%), hydrogenated at 80° C./10 bar. After 1 hour the hydrogenation was interrupted, the catalyst was filtered off and the filtrate was evaporated. After filtration over a silica gel column eluent hexane/AcOEt=9:1) there were obtained 2.4 g of S-(3-octylphenyl)dimethylthiocarbamate as a colourless oil.

c) 0.4 g of lithium aluminium hydride was suspended in 25 ml of THF. A solution of 2.4 g of S-(3-octylphenyl)dimethylthiocarbamate in 30 ml of THF was added dropwise thereto at 0° C. and the mixture was stirred at 0° C. for 2 hours. Subsequently, a solution of 1.2 g of s 3,3-dimethylallyl bromide in 10 ml of THF was added dropwise thereto and the mixture was stirred at 0° C. for a further 2 hours. The reaction mixture was poured on to ice-water, acidified with 6N hydrochloric acid, extracted with EtOEt, dried and evaporated. After filtration over a silica gel column (eluent hexane/AcOEt=4:1) there were obtained 2.3 g of 3-octylphenyl (3-methyl-2-butenyl) thioether as a colourless oil. This product was dissolved in 100 ml of toluene and, after the addition of 2 g of p-toluenesulphonic acid, heated to reflux for 20 hours on a water separator. After cooling the reaction mixture was neutralized by the addition of aqueous sodium bicarbonate solution and extracted with AcOEt. After filtration over a silica gel column (eluent hexane/AcOEt=9:1) there were obtained 2.1 g of 7-octyl-3,4-dihydro-4,4-dimethyl-2H-1-benzothiopyran as a pale yellowish oil.

d) 0.6 g of acetyl chloride was dissolved in 50 ml of methylene chloride and treated portionwise at 0° C. with 1 g of aluminium chloride. After 15 minutes a solution of 2.1 g of 7-octyl-3,4-dihydro-4,4-dimethyl-2H-1-benzothiopyran in 50 ml of methylene chloride was added dropwise thereto. The mixture was stirred at 0° C. for 2 hours, poured on to ice-water and extracted with methylene chloride. The crude product was purified by chromatography on a Lobar finished column (Merck) (eluent hexane/AcOEt 1%). There were obtained 1.3 g of 6-acetyl-7-octyl-3,4-dihydro-4,4-dimethyl-2H-1-benzothiopyran as a pale yellowish oil.

e) 1.3 g of 6-acetyl-7-octyl-3,4-dihydro-4,4-dimethyl-2H-1-benzothiopyran were dissolved in 100 ml of chloroform. At 0° C. there were added dropwise thereto firstly 1 equivalent (0.74 g) of 85% m-chloroperbenzoic acid dissolved in 50 ml of chloroform and after 2 hours a further equivalent of m-chloroperbenzoic acid. The mixture was stirred at 0° C. overnight, poured on to ice-water/sodium carbonate and extracted with methylene chloride. After recrystallization of the crude product from AcOEt/hexane there was obtained 1 g of 6-acetyl-7-octyl-3,4-dihydro-4,4-dimethyl-2H-1-benzothiopyran-1,1-dioxide in colourless crystals, m.p. 77°–78° C.

f) In an analogy to Example 1 g), by reacting 0.95 g of 6-acetyl-7-octyl-3,4-dihydro-4,4-dimethyl-2H-1-benzothiopyran-1,1-dioxide with 1.8 g of diethyl (4-carbethoxybenzyl)phosphonate, after deprotonization with sodium hydride in dimethyl sulphoxide and flash chromatography of the crude product on silica gel (hexane/AcOEt=1:1), there were isolated 1.3 g of ethyl 4-[2-(4,4-dimethyl-7-octyl-1,1-dioxo-3,4-dihydro-2H-1-benzothiopyran-6-yl)-propenyl]-benzoate as a pale yellow oil with an E/Z ratio of about 4:9. The E/Z ratio can be shifted in favour of the E isomer (E/Z~1:1) by irradiating the crude product in THF with a Hg high pressure lamp for 5 hours. By preparative HPLC (diisopropyl ether/hexane=55:45) of 0.9 g of E/Z mixture there were obtained 300 mg of the E isomer and 430 mg of the Z isomer as pale yellowish oils.

EXAMPLE 8

300 mg of ethyl 4-[2-(4,4-dimethyl-7-octyl-1,1-dioxo-3,4-dihydro-2H-1-benzothiopyran-6-yl)-propenyl]-benzoate were dissolved in 30 ml of ethanol. After the addition of a solution of 330 mg of potassium hydroxide in 10 ml of water the mixture was heated to 40° C. for 3 hours. The clear reaction mixture was poured on to ice-water, acidified with 3N hydrochloric acid and repeatedly extracted with AcOEt. After recrystallization of the crude product from AcOEt/hexane there were obtained 210 mg of (E)-4-[2-(4,4-dimethyl-7-octyl-1,1-dioxo-3,4-dihydro-2H-1-benzothiopyran-6-yl)-propenyl]-benzoic acid in white crystals, m.p. 176°–178° C.

EXAMPLE 9

1.84 g of 1-(1,1-dioxo-5,5-dimethyl-8-octyloxy-2,3,4,5-tetrahydro-1-benzothiepin-7-yl)-ethanol were placed in 20 ml of acetonitrile and treated with 1.84 g of triphenylphosphine hydrobromide. The mixture was heated under reflux for 65 hours, cooled and evaporated i.v. The residue was taken up in $CH_2Cl_2$, dried over $Na_2SO_4$ and again evaporated. Trituration in 100 ml of EtOEt/hexane (1:1) finally yielded 2.82 g of phosphonium salt as white crystals which were reacted as follows:

The crystals are dissolved in 25 ml of abs. THF under argon and deprotonized at 0° C. by the dropwise addition of 3.9 ml of 1.55M nBuLi (hexane). 814 mg of ethyl 4-formylbenzoate were added to the red ylid solution after 15 minutes and the mixture was left to react at 0° C. for 1 hour and at room temperature for 1 hour. Extraction with AcOEt, washing with water, drying, evaporation, flash chromatography on silica gel (hexane/AcOEt=85/15) and three-fold recrystallization from hexane/AcOEt finally gave 702 mg of methyl (E)-4-[2-(8-octyloxy-5,5-dimethyl-1,1-dioxo-2,3,4,5-tetrahydro-1-benzothiepin-7-yl)-propenyl]-benzoate as white crystals, m.p. 79°-80° C.

The 1-(1,1-dioxo-5,5-dimethyl-8-octyloxy-2,3,4,5-tetrahydro-1-benzothiepin-7-yl)-ethanol used as the starting material can be prepared as follows:

a) 16.9 g of methoxymethyltriphenylphosphonium chloride were placed in 100 ml of abs. THF and treated slowly at −5° C. under argon with 30 ml of 1.55M nBuLi. After 15 minutes a solution of 8.26 g of 8-bromo-2,3,4,5-tetrahydro-1-benzothiepin-5-one in 50 ml of THF was slowly added dropwise and the mixture was left to react for 2 hours. Then, the reaction mixture was partitioned between hexane and EtOH/water=8/2, the lighter phase was dried and evaporated i.v. There were obtained 9.1 g of crude enol ether mixture which was hydrolyzed in 70 ml of THF under argon using 70 ml of 35% $HClO_4$. After 2 hours at room temperature the mixture was poured on to ice, washed with water, dried and evaporated. Flash chromatography on silica gel (hexane/AcOEt=95/5) gave 6.86 g of 8-bromo-2,3,4,5-tetrahydro-1-benzothiepine-5-carbaldehyde as a colourless oil (91.5% pure according to GC).

b) 6.86 g of the aldehyde obtained in a) were placed in 70 ml of abs. tBuOH under argon and treated with 5.76 g of K tert.-butylate. The mixture was cooled to about 15° C. internal temperature and 4.3 ml of methyl iodide were slowly added dropwise. The mixture o was stirred for a further 2 hours, poured on to ice, extracted with EtOEt, washed with water and NaCl soln., dried and evaporated. Flash chromatography on silica gel (hexane/AcOEt=96/4) yields 3.24 g of α-methylated aldehyde as a colourless oil.

c) This 3.24 g of 8-bromo-5-methyl-2,3,4,5-tetrahydro-1-benzothiepine-5-carbaldehyde were placed in 45 ml of diethylene glycol and treated with 1.38 ml of hydrazine hydrate and 3.23 g of KOH pellets. The mixture was heated, firstly to 100° C. for 1 hour and subsequently to 180° C. for 3 hours. After cooling the mixture was poured on to ice, extracted with EtOEt, washed with water, dried and evaporated i.v. Flash chromatography on silica gel (hexane) gave 2.58 g of 8-bromo-5,5-dimethyl-2,3,4,5-tetrahydro-1-benzothiepine as colourless crystals, m.p. 81°-82° C.

d) 2.54 g of the above bromide were placed in 30 ml of abs. THF under argon and converted into the corresponding Li compound at −78° C. by the dropwise addition of 6.3 ml of 1.5M nBuLi. After 30 minutes 2.9 ml of anhydrous nitrobenzene were added thereto at −78° C. After 1 hour the mixture was poured on to ice, extracted with EtOEt, washed with water, dried and evaporated. Flash chromatography on silica gel (hexane/AcOEt, 95:5) yielded 1.08 g of 5,5-dimethyl-2,3,4,5-tetrahydro-1-benzothiepin-8-ol as a brownish oil.

e) 340 mg of NaH (about 50%) were placed in 10 ml of abs. DMF under argon. 1.08 g of 5,5-dimethyl-2,3,4,5-tetrahydro-1-benzothiepin-8-ol dissolved in 10 ml of abs. DMF were added dropwise thereto at 0° C. and the mixture was stirred for 30 minutes. Then, 1.36 g of 1-octyl bromide were added and the mixture was left to react at room temperature for 2 hours. The mixture was poured on to ice, extracted with EtOEt, washed with water, dried and evaporated. Flash chromatography on silica gel (hexane/AcOEt=99/1) yielded 1.60 g of 5,5-dimethyl-8-octyloxy-2,3,4,5-tetrahydro-1-benzothiepine as a colourless oil.

f) 0.86 ml of AcCl and 1.24 g of $AlCl_3$ were placed in 17 ml of $CH_2Cl_2$ under argon. 1.60 g of 5,5-dimethyl-8-octyloxy-2,3,4,5-tetrahydro-1-benzothiepine dissolved in 15 ml of $CH_2Cl_2$ were added dropwise thereto at −20° C. After 15 minutes the mixture was poured on to ice, extracted with EtOEt, washed with bicarbonate and NaCl solution, dried and evaporated. Flash chromatography on silica gel (hexane/AcOEt=95/5) yielded 1.97 g of 1-(5,5-dimethyl-8-octyloxy-2,3,4,5-tetrahydro-1-benzothiepin-7-yl)-ethanone as a colourless oil.

g) 1.93 g of 1-(5,5-dimethyl-8-octyloxy-2,3,4,5-tetrahydro-1-benzothiepin-7-yl)-ethanone were placed in 40 ml of $CH_2Cl_2$ and treated at −25° C. with 3.81 g of m-chloroperbenzoic acid (about 85%). The mixture was stirred at 0° C. for 2.5 hours, poured on to ice, extracted with AcOEt, washed in succession with pyrosulphite soln., 2N NaOH, water and NaCl soln., dried and evaporated. Flash chromatography on silica gel (hexane/AcOEt=8/2) gave 1.77 g of 1-(1,1-dioxo-5,5-dimethyl-8-octyloxy-2,3,4,5-tetrahydro-1-benzothiepin-7-yl)-ethanone as a colourless oil.

h) 1.77 g of 1-(1,1-dioxo-5,5-dimethyl-8-octyloxy-2,3,4,5-tetrahydro-1-benzothiepin-7-yl)-ethanone were dissolved in 15 ml of EtOH and treated with 1.68 mg of $NaBH_4$. After 2 hours the mixture was poured on to ice, extracted with AcOEt, washed with water, dried and evaporated. There were thus obtained 1.84 g of 1-(1,1-dioxo-5,5-dimethyl-8-octyloxy-2,3,4,5-tetrahydro-1-benzothiepin-7-yl)-ethanol as a colourless oil which was uniform according to TLC.

EXAMPLE 10

In analogy to Example 9 there were manufactured:
Methyl (E)-4-[2-(8-hexyloxy-5,5-dimethyl-1,1-dioxo-2,3,4,5-tetrahydro-1-benzothiepin-7-yl)-propenyl]-benzoate as white crystals, m.p. 107.5°-108.5° C.;
methyl (E)-4-[2-(8-heptyloxy-5,5-dimethyl-1,1-dioxo-2,3,4,5-tetrahydro-1-benzothiepin-7-yl)-propenyl]-benzoate as white crystals, m.p. 92°-93° C.

EXAMPLE 11

193 mg of methyl (E)-4-[2-(8-heptyloxy-5,5-dimethyl-1,1-dioxo-2,3,4,5-tetrahydro-1-benzothiepin-7-yl)- propenyl]-benzoate were placed in 2 ml of THF/EtOH (1:1) and treated with 0.37 ml of 3N NaOH. The mixture was stirred at room temperature overnight, poured on to ice, extracted with AcOEt, washed with a small amount of water, dried and evaporated i.v. Crystallization from AcOEt yielded 152 mg of (E)-4-[2-(8-heptyloxy-5,5-dimethyl-1,1-dioxo-2,3,4,5-tetrahydro-1-benzothiepin-7-yl)-propenyl]-benzoic acid as white crystals, m.p. 153°–154° C.

EXAMPLE 12

In analogy to Example 11 there were manufactured:
(E)-4-[2-(8-Hexyloxy-5,5-dimethyl-1,1-dioxo-2,3,4,5-tetrahydro-1-benzothiepin-7-yl)-propenyl]-benzoic acid as white crystals, m.p. 157°–158° C.; and
(E)-4-[2-(8-octyloxy-5,5-dimethyl-1,1-dioxo-2,3,4,5-tetrahydro-1-benzothiepin-7-yl)-propenyl]-benzoic acid as white crystals, m.p. 168°–169° C.

EXAMPLE 13

3.58 g of 1-(5,5-dimethyl-8-octyl-1,1-dioxo-2,3,4,5-tetrahydro-1-benzothiepin-7-yl)-ethanol were placed in 20 ml of acetonitrile and treated with 3.34 g of triphenylphosphine hydrobromide. The mixture was heated under reflux for 70 hours, cooled and evaporated i.v. The residue was taken up in $CH_2Cl_2$, dried over $Na_2SO_4$ and again evaporated. Trituration in 200 ml of EtOEt/hexane (1:1) finally yielded 5.67 g of phosphonium salt as white crystals. This phosphonium salt was dissolved in 80 ml of abs. THF under argon and deprotenized at 0° C. by the dropwise addition of 7.45 ml of 1.55M nBuLi. After 15 minutes 1.60 g of methyl 4-formylbenzoate were added thereto and the mixture was left to react at room temperature for 1 hour. Extraction with AcOEt, washing with water, drying, evaporation, flash chromatography on silica gel (hexane/AcOEt=80/20) and two-fold recrystallization from hexane/AcOEt finally gave 1.41 g of methyl (E)-4-[2-(5,5-dimethyl-8-octyl-1,1-dioxo-2,3,4,5-tetrahydro-1-benzothiepin-7-yl)-propenyl]-benzoate as white crystals, m.p. 85°–86° C.

The 1-(5,5-dimethyl-8-octyl-1,1-dioxo-2,3,4,5-tetrahydro-1-benzothiepin-7-yl)-ethanol used as the starting material was prepared as follows:

a) The corresponding Grignard compound was prepared from 3.00 g of 8-bromo-5,5-dimethyl-2,3,4,5-tetrahydro-1-benzothiepine and 340 mg of Mg shavings in 30 ml of abs. THF under argon. After cooling to −20° C. there were added thereto 220 mg of purified CuI followed by 3.18 ml of 1-iodooctane. The mixture was warmed to 0° C. and, after 1.5 hours, poured into ice/$NH_4Cl$ solution. Extraction with EtOEt, washing with water and NaCl solution, drying, evaporation and flash chromatography on silica gel (hexane) yielded 2.56 g of 5,5-dimethyl-8-octyl-2,3,4,5-tetrahydro-1-benzothiepine as a colourless oil.

b) As described under Example 9f), g) and h), this 5,5-dimethyl-8-octyl-2,3,4,5-tetrahydro-1-benzothiepine was acetylated, oxidized to the sulphone and finally reduced with $NaBH_4$ to 1-(5,5-dimethyl-8-octyl-1,1-dioxo-2,3,4,5-tetrahydro-1-benzothiepin-7-yl)-ethanol.

EXAMPLE 14

In analogy to Example 11 there was manufactured:
(E)-4-[2-(5,5-Dimethyl-8-octyl-1,1-dioxo-2,3,4,5-tetrahydro-1-benzothiepin-7-yl)-propenyl]-benzoic acid as white crystals, m.p. 164°–165° C.

EXAMPLE 15 a) 2.20 g of 1-(5,5-dimethyl-8-hexyloxy-2,3,4,5-tetrahydro-1-benzothiepin-7-yl)-ethanone, prepared in analogy to Example 9f), were placed in 20 ml of abs. THF under argon and treated at −20° C. with 9.9 ml of 1M vinylmagnesium bromide solution (THF). After completion of the addition (clearly exothermic) the mixture was left to react for 1 hour and then poured on to ice/$NH_4Cl$. Extraction with EtOEt, washing with saturated NaCl solution, drying and evaporation followed by flash chromatography on silica gel (hexaneAcOEt=95/5) gave 2.16 g of tertiary alcohol as a colourless oil.

b) The foregoing alcohol was dissolved in 15 ml of acetonitrile and treated with 2.45 g of triphenylphosphine hydrobromide. The mixture was stirred at room temperature overnight, the solvent was removed i.v. and the residue was taken up in $CH_2Cl_2$. Drying, evaporation and digestion in 200 ml of EtOEt/hexane=1/1 yielded 4.14 g of rearranged phosphonium salt as a pink solid.

c) 4.14 g of the phosphonium salt were placed in 20 ml of 1,2-butylene oxide and treated with 691 mg of ethyl (E)-3-formylcrotonate. The mixture was heated to reflux for 1 hour, cooled, poured on to ice and extracted with EtOEt. Washing with water and saturated NaCl solution drying, evaporation and flash chromatography on silica gel (hexane/AcOEt=96/4) yielded 2.58 g of triene ester which was isomerized largely to the all-trans compound as follows:

d) 2.58 g of the reiene ester were dissolved in 25 ml of acetonitrile under argon and 37 mg of Pd(II) nitrate, 134 mg of triphenylphosphine and 35 microlitres of triethylamine were added thereto. The mixture was stirred at 50° C. for 4 hours and worked up. Renewed flash chromatography on silica gel (hexane AcOEt=96/4) yielded 2.33 g of almost isomer-pure ethyl (2E,4E,6E)-7-(8-hexyloxy-5,5-dimethyl-2,3,4,5-tetrahydro-1-benzothiepin-7-yl)-3-methyl-octa-2,4,6-trienoate as a pale yellow oil which was oxidized to the sulphone as follows:

e) The ester was placed in 75 ml of $CH_2Cl_2$ and the solution was treated at −20° C. with 2.4 eq. of m-chloroperbenzoic acid. The mixture was allowed to warm to 0° C. and the reaction was followed by thin-layer chromatography. After 2 hours the mixture was poured on to ice, extracted with AcOEt, washed in succession with Na pyrosulphite solution, 2N NaOH and NaCl solution, dried and evaporated. Medium pressure chromatography on silica gel (hexane/AcOEt=85/15) followed by recrystallization from hexane/AcOEt finally yielded 760 mg of ethyl (2E,4E,6E)-7-(8-hexyloxy-5,5-dimethyl-1,1-dioxo-2,3,4,5-tetrahydro-1-benzothiepin-7-yl)-3-methyl-octa-2,4,6-trienoate as colourless crystals of melting point 116°–120° C. (dec.). Moreover, 170 mg of the over-oxidized 6,7-epoxy derivative were obtained.

EXAMPLE 16

In analogy to Example 15 there was manufactured:

Ethyl (2E,4E,6E)-7-(8-heptyloxy-5,5-dimethyl-1,1-dioxo-2,3,4,5-tetrahydro-1-benzothiepin-7-yl)-3-methyl-octa-2,4,6-trienoate as pale yellow crystals of m.p. 98°–99° C.

EXAMPLE 17

254 mg of ethyl (2E,4E,6E)-7-(8-hexyloxy-5,5-dimethyl-1,1-dioxo-2,3,4,5-tetrahydro-1-benzothiepin-7-yl)-3-methyl-octa-2,4,6-trienoate were placed in 2 ml of EtOH/THF=1/1 and treated with 0.5 ml of 3N NaOH. The mixture was stirred overnight, poured on to ice, acidified with conc. HCl, extracted with AcOEt, washed with a small amount of water, dried and evaporated i.v. Crystallization from AcOEt/hexane yielded 139 mg of (2E,4E,6E)-7-(8-hexyloxy-5,5-dimethyl-1,1-dioxo-2,3,4,5-tetrahydro-1-benzothiepin-7-yl)-3-methyl-octa-2,4,6-trienoic acid as colourless crystals, m.p. 164°–165° C.

EXAMPLE 18

In analogy to Example 17 there was manufactured: (2E,4E,6E)-7-(8-Heptyloxy-5,5-dimethyl-1,1-dioxo-2,3,4,5-tetrahydro-1-benzothiepin-7-yl)-3-methyl-octa-2,4,6-trienoic acid as pale yellow crystals of m.p. 152°–153° C.

EXAMPLE 19

In analogy to Example 15 there was manufactured: Ethyl (2E,4E,6E)-7-(5,5-dimethyl-1,1-dioxo-2,3,4,5-tetrahydro-8-octyl-1-benzothiepin-7-yl)-3-methyl-octa-2,4,6-trienoate as colourless crystals of m.p. 88°–89° C.

EXAMPLE 20

In analogy to Example 17 there was manufactured: (2E,4E,6E)-7-(5,5-Dimethyl-1,1-dioxo-2,3,4,5-tetrahydro-8-octyl-1-benzothiepin-7-yl)-3-methyl-octa-2,4,6-trienoic acid as pale yellow crystals of m.p. 104°–105° C.

EXAMPLE 21

In analogy to Example 9 there was manufactured: Methyl (E)-4-[2-(6-heptyloxy-3,3-dimethyl-1,1-dioxo-2,3-dihydro-benzo[b]thiophen-5-yl)propenyl]-benzoate as white crystals of m.p. 95°–96° C.

The 6-bromo-3,3-dimethyl-2,3-dihydrobenzo[b]thiophene used as the starting material was synthesized as follows:

17.08 g of 3-bromothiophenol were placed in 60 ml of acetone and treated at 0° C. with 37.3 g of powdered $K_2CO_3$. Then, 10.1 ml of ethyl bromoacetate were slowly added dropwise thereto and the mixture was left to react for 1 hour. Subsequently, the mixture was poured on to ice, extracted with EtOEt, washed with water, dried over $Na_2SO_4$ and evaporated. There were thus obtained 24.05 g of product (GC>98%), which was processed as follows:

The corresponding Grignard compound was prepared from 5.46 g of Mg shavings and 14.5 ml of MeI in 150 ml of abs. EtOEt under argon according to the standard procedure. 22.8 g of the ester prepared above, dissolved in 70 ml of abs. EtOEt, were added dropwise thereto at −10° C. After 1 hour the mixture was poured on to ice/$NH_4Cl$, extracted with EtOEt, washed with sat. NaCl solution, dried over $Na_2SO_4$ and evaporated. Flash chromatography on silica gel (hexane/AcOEt=85/15) gave 11.94 g of tertiary alcohol which was cyclized as follows:

21.7 g of $AlCl_3$ were placed in 80 ml of $CS_2$ under argon. 11.94 g of the tertiary alcohol prepared above, dissolved in 10 ml of $CS_2$, were added dropwise at 0° C. while stirring. The mixture was heated to reflux for 3 hours, cooled, poured cautiously on to ice and extracted with hexane. The organic phase was washed with water, dried over $Na_2SO_4$ and the solvent was removed i.v. Flash chromatography on silica gel (hexane) yielded 9.54 g of a mixture which according to GC contained 36.5% of the desired 6-bromo-3,3-dimethyl-2,3-dihydro-benzo[b]thiophene and 60% of the regioisomeric 4-bromo compound. Separation was effected at the next stage, after conversion into the corresponding phenols, which was carried out as described under Example 9d).

EXAMPLE 22

In analogy to Example 11 there was manufactured: (E)-4-[2-(6-Heptyloxy-3,3-dimethyl-1,1-dioxo-2,3-dihydrobenzo[b]thiophen-5-yl)propenyl]-benzoic acid as white crystals of m.p. 151°–152° C.

Example A

Hard gelatine capsules can be produced as follows:

| Ingredients | mg/capsule |
|---|---|
| 1. Spray-dried powder containing 75% of compound I | 20 |
| 2. Sodium dioctylsulphosuccinate | 0.2 |
| 3. Sodium carboxymethylcellulose | 4.8 |
| 4. Microcrystalline cellulose | 86.0 |
| 5. Talc | 8.0 |
| 6. Magnesium stearate | 1.0 |
| Total | 120 |

The spray-dried powder, which is based on the active ingredient, gelatine and microcrystalline cellulose and which has an average particle size of the active ingredient of <1µ (measured by means of autocorrelation spectroscopy), is moistened with an aqueous solution of sodium carboxymethylcellulose and sodium dioctylsulphosuccinate and kneaded. The resulting mass is granulated, dried and sieved, and the granulate obtained is mixed with microcrystalline cellulose, talc and magnesium stearate. The powder is filled into size 0 capsules.

Example B

Tablets can be produced as follows:

| Ingredients | mg/tablet |
|---|---|
| 1. Compound I as a finely milled powder | 20 |
| 2. Powd. lactose | 100 |
| 3. White corn starch | 60 |
| 4. Povidone K30 | 8 |
| 5. White corn starch | 112 |
| 6. Talc | 16 |
| 7. Magnesium stearate | 4 |
| Total | 320 |

The finely milled active ingredient is mixed with lactose and a portion of the corn starch. The mixture is moistened with an aqueous solution of Povidone K30 and kneaded, and the resulting mass is granulated, dried and sieved. The granulate is mixed with the remaining corn starch, talc and magnesium stearate and pressed to tablets of suitable size.

Example C

Soft gelatine capsules can be prepared as follows:

| Ingredients | mg/capsule |
|---|---|
| 1. Compound I | 5 |
| 2. Triglyceride | 450 |
| Total | 455 |

10 g of compound I are dissolved in 90 g of medium-chain triglyceride while stirring and under inert gasification and protection from light. The solution is processed as a capsule fill mass to soft gelatine capsules containing 5 mg of active ingredient.

Example D

A lotion can be produced as follows:

| Ingredients | |
|---|---|
| 1. Compound I finely milled | 1.0 g |
| 2. Carbopol 934 | 0.6 g |
| 3. Sodium hydroxide | q.s. ad pH 6 |
| 4. Ethanol, 94% | 50.0 g |
| 5. Demineralized water | ad 100.0 g |

The active ingredient is incorporated into the 94% ethanol/water mixture with protection from light. Carbopol 934 is stirred in until gelling is complete and the pH value is adjusted with sodium hydroxide.

We claim:

1. A fused bicyclic compound of the formula:

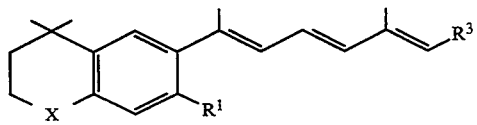

I-A wherein X is —S—, —SO— or —SO$_2$—; R$^1$ is C$_{7\text{-}10}$-alkyl or C$_{7\text{-}10}$-alkoxy; and R$^3$ is carboxy or lower-alkoxycarbonyl;
or salts of said bicyclic compound when R$^3$ is carboxy.

2. A fused bicyclic compound of the formula:

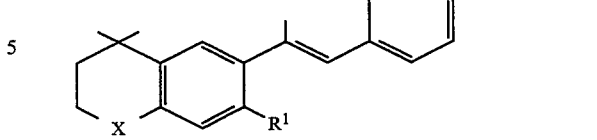

I-B wherein X is —S—, —SO— or —SO$_2$—; R$^1$ is C$_{7\text{-}10}$-alkyl or C$_{7\text{-}10}$-alkoxy; and R$^3$ is carboxy or lower-alkoxycarbonyl;
or salts of said bicyclic compound when R$^3$ is carboxy.

3. The compound of claim 1 wherein X is —S—.

4. The compound of claim 3 wherein said compound is ethyl-7-[7-heptyloxy-3,4-dihydro-4,4-dimethyl-2H-1-benzothiopyran-6-yl]-3-methyl-octa-2,4,6-trienoate.

5. The compound of claim 3 wherein said compound is 7-[7-heptyloxy-3,4-dihydro-4,4-dimethyl-2H-1-benzothiopyran-6-yl]-3-methyl-2,4,6-octatrienoic acid.

6. The compound of claim 3 wherein X is —SO—.

7. The compound of claim 6 wherein said compound is 7-[7-heptyloxy-1-oxo-3,4-dihydro-4,4-dimethyl-2H-1-benzothiopyran-6-yl]-3-methyl-octa-2,4,6-trienoic acid.

8. The compound of claim 1 wherein X is —SO$_2$—.

9. The compound of claim 8 wherein said compound is 7-[7'-(heptyloxy)-3',4'-dihydro-4',4'-dimethyl-2'H-1-benzothiopyran-6'-yl)-3-methyl-2,4,6-octatrienoic acid 1',1'-dioxide.

10. The compound of claim 2 wherein said compound is ethyl p-2-[3',4'-dihydro-4',4'-dimethyl-7'-(heptyloxy)-2'H-1-benzothiopyran-6'-yl]propenyl]benzoate 1',1'-dioxide.

11. The compound of claim 2 wherein said compound is p-[(Z)-2-[3',4'-dihydro-4',4'-dimethyl-7'-(heptyloxy)-2'H-1-benzothiopyran-6'-yl]propenyl]benzoic acid 1',1'-dioxide.

12. The compound of claim 2 wherein said compound is p-[(E)-2-[3',4'-dihydro-4',4'-dimethyl-7'-(heptyloxy)-2'H-1-benzothiopyran-6'-yl]propenyl]benzoic acid 1',1'-dioxide.

13. The compound of claim 2 wherein said compound is ethyl (Z)-4-[2-(4,4-dimethyl-7-octyl-1,1-dioxo-3,4-dihydro-2H-1-benzothiopyran-6-yl)-propenyl]-benzoate.

14. The compound of claim 2 wherein said compound is ethyl (E)-4-[2-(4,4-dimethyl-7-octyl-1,1-dioxo-3,4-dihydro-2H-1-benzothiopyran-6-yl)-propenyl]-benzoate.

15. The compound of claim 2 wherein said compound is 4-[2-(4,4-dimethyl-7-octyl-1,1-dioxo-3,4-dihydro-2H-1-benzothiopyran-6-yl)-propenyl]-benzoic acid.

* * * * *